(12) United States Patent
Self et al.

(10) Patent No.: US 8,389,296 B2
(45) Date of Patent: Mar. 5, 2013

(54) ASSAY DEVICES AND METHODS AND COMPONENTS FOR USE THEREIN

(75) Inventors: Colin Henry Self, Ponteland (GB); Michael Chard, County Durham (GB)

(73) Assignee: Selective Antibodies Limited, Newcastle Upon Tyne (GB)

( * ) Notice: Subject to any disclaimer, the term of this patent is extended or adjusted under 35 U.S.C. 154(b) by 161 days.

(21) Appl. No.: 12/593,262

(22) PCT Filed: Apr. 22, 2008

(86) PCT No.: PCT/GB2008/001430
§ 371 (c)(1),
(2), (4) Date: Mar. 22, 2010

(87) PCT Pub. No.: WO2008/129302
PCT Pub. Date: Oct. 30, 2008

(65) Prior Publication Data
US 2010/0209295 A1    Aug. 19, 2010

(30) Foreign Application Priority Data
Apr. 23, 2007 (GB) .................................. 0707870.2

(51) Int. Cl.
*G01N 33/558* (2006.01)
(52) U.S. Cl. ..... 436/514; 422/420; 422/425; 435/287.1; 435/287.7; 435/970; 436/518; 436/810
(58) Field of Classification Search ............... 435/283.1, 435/287.1, 287.7, 970; 436/514, 518, 810; 422/420, 425
See application file for complete search history.

(56) References Cited

U.S. PATENT DOCUMENTS

| | | | |
|---|---|---|---|
| 4,959,305 A | 9/1990 | Woodrum et al. | |
| 5,451,504 A | 9/1995 | Fitzpatrick et al. | |
| 5,641,690 A | 6/1997 | Self | |
| 5,942,407 A | 8/1999 | Liotta et al. | |
| 6,514,773 B1 | 2/2003 | Klein et al. | |
| 2005/0208529 A1* | 9/2005 | Winther et al. | 435/6 |
| 2006/0246506 A1 | 11/2006 | Pulli et al. | |

FOREIGN PATENT DOCUMENTS

| | | |
|---|---|---|
| EP | 0264219 A2 | 4/1988 |
| EP | 0279097 A2 | 8/1988 |
| EP | 1416275 | 5/2004 |
| WO | WO-85-04422 A1 | 10/1985 |
| WO | WO-86-00140 A1 | 1/1986 |
| WO | WO-88-00240 A1 | 1/1988 |
| WO | WO 88/08534 * | 11/1988 |
| WO | WO 92-19973 | 11/1992 |
| WO | WO 95-04231 | 2/1995 |
| WO | WO-99-18436 A | 4/1999 |
| WO | WO-00-00826 A1 | 1/2000 |

(Continued)

OTHER PUBLICATIONS

PCT/GB08/001430 Search Report dated Sep. 9, 2008.

(Continued)

*Primary Examiner* — Chris L Chin
(74) *Attorney, Agent, or Firm* — Wilson, Sonsini, Goodrich & Rosati

(57) ABSTRACT

Dipsticks and other assay devices suitable for the assay of haptens are disclosed. Also disclosed are blocking agents for use in such devices.

31 Claims, 1 Drawing Sheet

FOREIGN PATENT DOCUMENTS

Figure 1:
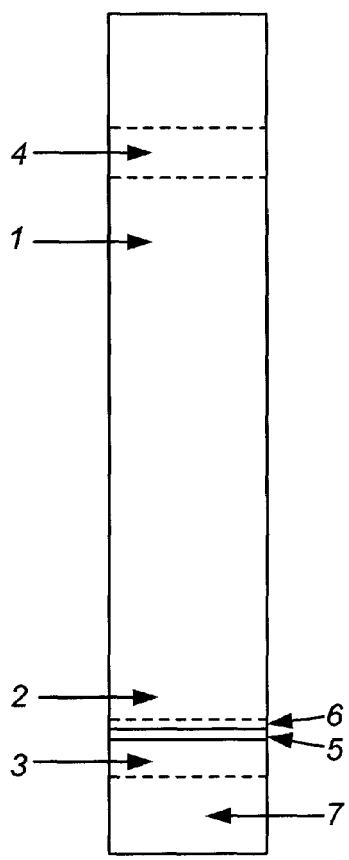
Figure 2:
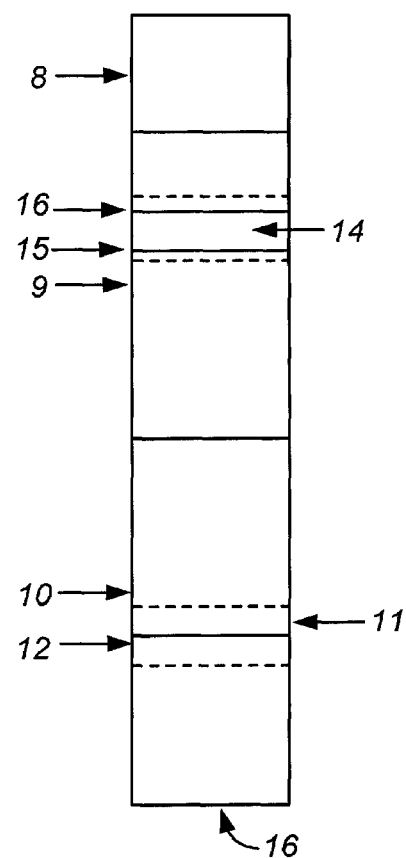

| WO | WO-00-15020 A | 3/2000 |
|----|---------------|--------|
| WO | WO-2005-022150 | 3/2005 |
| WO | WO-2005-083431 A2 | 9/2005 |

OTHER PUBLICATIONS

Ashton, "Measurements in miniature," RSC/Advancing the Chemical Sciences, Chemistry World, Royal Society of Chemistry, 2007, pp. 1-4.

Barnard et al., "The Measurement of Oestrone-3-glucuronide in Urine by Non-Competitive Idiometric Assay," J. Steroid Biochem. Molec. Biol. 55(1):107-114 (1995).

Kobayashi et al., "Idiotype-anti-idiotype-based noncompetitive enzyme-linked immunosorbent assay of ursodeoxycholic acid 7-N-acetylglucosamides in human urine with subfemtomole rangesensitivity," J. Immunol. Methods 272:1-10 (2003).

Mares et al., "A direct non-competitive idiometric enzyme immunoassay for serum oestradiol," J. Immunol. Methods 181:83-90 (1995).

Self, C., "2 Non-Competitive Immunoassays for Small Molecules—The Anti-Complex, Selective Antibody and Apposition Systems," *The Immunoassay Handbook*, Third Edition, D. Wild (ed.), 2005, pp. 41-47.

Woods, "Noncompetitive Immunofluorometric Methods for Steroids," *Principles and Practice of Immunoassay*, Second Edition, Price and Newman, eds., 1991, pp. 402-404.

Barnard et al., "The measurement of progesterone in serum by a non-competitive idiometric assay," Steroids 60:824-829 (1995).

Barnard et al., "Idiometric Assay: Noncompetitive Immunoassay for Small Molecules Typified by the Measurement of Estradiol in Serum," Clinical Chemistry 36(11):1945-1950 (1990).

Kobayashi et al., "Monoclonal anti-idiotype antibodies recognizing the variable region of a high-affinity antibody against 11-deoxycortisol. Production, characterization and application to a sensitive noncompetitive immunoassay," J. Immunol. Methods 274:63-75 (2003).

Kobayashi, N. And Goto, J., "Noncompetitive immunoassays for small molecules with high sensitivity and specificity," Advances in Clinical Chemistry 36:139-171 (2001).

Niwa et al., "An enzyme-linked immunometric assay for cortisol based on idiotype-anti-idiotype reactions," Analytica Chimica Acta 638:94-100 (2009).

Piran et al., "New Noncompetitive Immunoassays of Small Analytes," Clinical Chemistry 41(7):986-990 (1995).

Agrochemical Desk Reference $2^{nd}$ Ed, JH Montgomery, CRC Press LLC, (1997) 7 pgs.

GB 1010247.3 Search and Examination Report dated Mar. 21, 2011.
GB 1010247.3 Examination Report dated Jul. 25, 2011.
GB 1010247.3 Grant Notification dated Nov. 22, 2011.

* cited by examiner

ASSAY DEVICES AND METHODS AND COMPONENTS FOR USE THEREIN

This application is a section 371 national phase application of PCT/GB2008/001430, filed Apr. 22, 2008, which claims priority to UK patent application 0707870.2, filed Apr. 23, 2007; all of which are incorporated herein by reference in their entirety.

FIELD OF THE INVENTION

The present invention relates to assay devices, to methods of assaying haptens and to components useful in such devices and methods. More specifically this invention relates to assay devices using permeable materials, optionally in the form of dick sticks, to methods of use of such devices in the qualitative or quantitative determination of haptens and to chemical entities useful in such devices and methods.

BACKGROUND TO THE INVENTION

A common problem encountered in the assay of haptens is that standard competitive assays produce a signal in inverse proportion to the amount of hapten in the sample suspected of containing the hapten. Thus for when testing a sample that is free of analyte a strong signal is produces whereas when testing a sample containing a significant quantity of the hapten a weak signal is produced. This can lead to difficulty in using such a test in field conditions (for example in the outdoors) and even under laboratory conditions. Also such tests need to contain a control line that can take a prolonged time to develop so that the result of the assay can be confirmed. A solution to this problem was first suggested in U.S. Pat. No. 5,641,690 where it was proposed to employ an additional antibody in the system so that a positive read out could be obtained (that is one where the grated amount of hapten in the sample the greater the signal produced).

The system described in U.S. Pat. No. 5,641,690 potentially offered a major improvement but unfortunately has not been commercialised. This has been due in part to considerable difficulties resulting from the need to prepare a specific antibody against the primary antibody in the system for each analyte envisaged. Also the backgrounds generally encountered with the embodiments of U.S. Pat. No. 5,641,690 have tended to have rendered the results less than desirable in commercial use. Furthermore no working examples of lateral flow assays (such as dip sticks) have ever been shown to work employing the system of U.S. Pat. No. 5,641,690.

Methods which result in an assay which result in the measuring of the number of binding sites not occupied by analyte are described in WO95/04231 and WO92/19973.

There is therefore a continuing need to provide an assay for a hapten in which the signal increases as the concentration of the hapten in the sample being tested increases especially one which can be produced without need to produce a new specific antibody for each analyte as part of the signal generating system and preferably which can be formatted as a lateral flow assay such as a dip stick. Such an assay has now been found as have devices for performing the assay and components to use in the assay.

BRIEF DESCRIPTION OF THE INVENTION

The present invention provides an assay device which comprises a permeable material such that when as aqueous liquid is contacted with a first part of the permeable material it permeates to a second part of the permeable material, said permeable material having a first zone and a second zone disposed so that when the aqueous liquid is contacted with the first part of the permeable material it passes first through the first zone and then into the second zone as it permeates to the second part of the permeable material;

said first zone containing a signal generating means labelled with an antibody against a hapten;

said first zone also containing a binding material for said antibody against the hapten;

said second zone contains a locating means for said antibody against the hapten such that it binds to the antibody present on the signal generating means labelled with an antibody which has bound hapten but does not bind to antibody present on the signal generating means which has bound the binding material for said antibody against the hapten;

the signal generating means being such that a signal is generated on binding to said locating means; wherein:

(a) the locating means is not a specific binder for the antibody against the hapten and/or (b) the locating means is an antibody against the Fc region of the antibody against the hapten and/or (c) the binding material for the antibody against the hapten is free of hapten and/or hapten analogue and/or (d) the binding material is hapten or close structural analogue covalently bound to a synthetic hydrophilic molecule of molecular weight greater than 2000 and/or (e) the binding material has two hapten or close structural analogues.

Such devices may be used to determine whether a hapten is present in a sample suspected of containing it and may also be adapted to provide a qualitative measurement of the amount of hapten present.

The assay device is preferably in the form of a dip stick, for example in which the first zone is located towards one end of the dip stick and the second zone is located towards the other end of the dip stick.

The permeable material may be any material that allows the permeation of an aqueous liquid, for example water, urine, saliva, blood or plasma. Such materials can be visibly fibrous, for example such as filter papers, or can be visibly non fibrous, for example cellulose membranes. Permeable membranes for use in assay devices are well known to the skilled worker.

The signal generating means may be any that is visualised on concentration. Apt signal generating means include microparticles, for example of polymer or of metal. A preferred signal generating means are coloured latex and gold microparticles of which gold is presently most preferred. The use of gold sols in assay devices such as lateral flow devices are well known to the skilled worker.

The antibody against the hapten may be attached to the signal generating means in any suitable manner, for example as well understood by the skilled worker for attaching antibodies to gold microparticles.

The antibody against the hapten may be a monoclonal or polyclonal antibody. Surprisingly it has been found that polyclonal antibodies are particularly effective in the devices of this invention which, owing to their ready availability, provides an additional advantage to the invention.

The locating means is preferably not a specific antibody against the antibody against the hapten as this offers a greatly simplified method of putting the invention into operation. The locating means is favourably an antibody against the Fc region of the antibody against the hapten. Preferably the locating means is an anti IgG antibody. This may be a monoclonal or polyclonal antibody but it is particularly preferred that it is a polyclonal antibody.

The binding material against the antibody against the hapten is any which can compete with the hapten for the antibody against the hapten. Generally it is the hapten or a close structural analogue of the hapten covalently bound to a molecule that prevents the binding material binding to the locating means when the binding material is bound to the antibody against the hapten. Aptly the molecule to which the hapten or close structural analogue is covalently bound is a large molecule, for example has a molecular weight of 5000 daltons or more. Suitable large molecules include peptides, especially proteins, carbohydrates, and synthetic molecules, for example polymers. Favourably the large molecule is hydrophilic, for example polyethylene glycol or modified polyethylene glycol having terminal amino groups. Preferably the binding means will have been rendered free of hapten or hapten analogue by exhaustive dialysis. Most aptly the binding means has two or more, preferably two, hapten or close structural analogues therein.

The locating means is favourably not an antibody specific to the antibody against the hapten. The locating means is aptly a non-specific antibody, especially against the Fc region of the antibody against the hapten. Preferably the locating means is an anti IgG antibody. Although the locating means may be monoclonal it is preferably polyclonal.

The permeable material may be any that permits the movement of the signal generating means to which hapten or binder is bound through the material to the second zone, Such materials include papers such as filter paper and cellulose membranes, particularly nitrocellulose membranes. Often the device may be comprised of two or more permeable materials. Thus for example a paper may be joined to a cellulose membrane. In such an arrangement the first zone may be on the paper and the second zone may be on a nitrocellulose membrane.

In use the assay device is employed by applying an aqueous sample suspected of containing the hapten to a part of the permeable material so that the aqueous liquid permeates first through the first zone and then into the second zone. A detectable signal is produced if the sample contains hapten but not if the sample does not contain hapten. The intensity of the signal increases with the concentration of the hapten in the sample.

The assay device may be in any suitable geometrical format but that of a dip stick is preferred, that is a device that is longer than it is wide.

If desired the device may be adapted to detect hapten from surfaces, for example from skin. Suitable methods of achieving this are described in the general and patent literature, for example U.S. Pat. No. 6,514,773 may be consulted for suitable methods.

DESCRIPTION OF THE DRAWINGS

FIG. 1 shows an assay device of the invention in the form of a dip stick. The dip stick has a permeable layer of nitrocellulose (1) and a permeable layer of paper (2). On the paper layer is a first zone (3) and on the nitrocellulose layer is a second zone (4). The first zone contains a line (5) impregnated with gold labeled with an antibody against the hapten to be analysed, and a line (6) impregnated with binder for the antibody. The second zone (4) contains a non specific antibody against the antibody against the hapten to be analysed. The non-specific antibody will not bind to the antibody against the hapten if it has bound binder. The first zone is placed so as to allow sufficient area for addition of sample in a portion (7) downstream of the first zone. The sample addition portion (7) is impregnated with buffer.

FIG. 2 shows an alternative assay device of the invention in which films (8, 9 and 10) of paper (8), nitrocellulose (9) and again glass fiber (10) are employed. The paper film (8) contains the first zone (11) which is comprised of a line (12) impregnated with gold labelled with the antibody against the hapten and binder (13). The line (12) also contains gold labelled with biotin. The middle film (9) contains the second zone (14) which contains a line (15) of non-specific binder against the antibody labelled on the gold and a line (16) containing an antibody to biotin. The films (8, 9 and 10) are mounted on a Mylar® backing (16).

DETAILED DESCRIPTION OF THE INVENTION

The present invention provides an assay device which comprises a permeable material such that when as aqueous liquid is contacted with a first part of the permeable material it permeates to a second part of the permeable material, said permeable material having a first zone and a second zone disposed so that when the aqueous liquid is contacted with the first part of the permeable material it passes first through the first zone and then into the second zone as it permeates to the second part of the permeable material;

said first zone containing a signal generating means labelled with an antibody against a hapten;

said first zone also containing a binding material for said antibody against the hapten;

said second zone contains a locating means for said antibody against the hapten such that it binds to the antibody present on the signal generating means labelled with an antibody which has bound hapten but does not bind to antibody present on the signal generating means which has bound the binding material for said antibody against the hapten;

the signal generating means being such that a signal is generated on binding to said locating means; wherein:

(a) the locating means is not a specific binder for the antibody against the hapten and/or (b) the locating means is an antibody against the Fc region of the antibody against the hapten and/or (c) the binding material for the antibody against the hapten is free of hapten and/or hapten analogue and/or (d) the binding material is hapten or close structural analogue covalently bound to a synthetic hydrophilic molecule of molecular weight greater than 2000 and/or (e) the binding material has two hapten or close structural analogues.

In a presently preferred form the device is one wherein the locating means is a non-specific antibody.

(1) The Device.

The device may be in any format that permits lateral flow between the area to which the sample is introduced, the first zone and the second zone. A preferred form of the device will be a "dip stick". The skilled worker will be aware of many forms of dip stick described in the patent and general literature and many that have been commercialized, at least on a small scale. Such known formats may be employed in this invention since the surprising features of this invention relate to the reagents that are added to the dip stick rather than the physical construction of dip sticks themselves (however as will be seen below some particularly preferred forms of the dip stick are independently inventive).

A favoured form of the dip stick will be an elongate strip that is longer than it is wide. Such a dipstick will normally be rectangular. The length of the dipstick will generally be from 15 mm to 100 mm, for example at least 18, 20, 25, 30, 40, 50, 60, 70, 80 or 90 mm and less than 70, 60, 50, 45, 40, 35, 30, 25, 20 mm. Suitable widths for the dip stick will be from 10 to 50 mm (although on some occasions wider dipsticks can be used) for example about 12, 13, 15, 17, 20, 22, 25, 30, 35, 40 or 45 mm. An apt width is 25 mm owing to availability from manufactures in reel form. Generally the operative area of the dipstick (the area in use rather than additional area not needed for operation but present for reasons of aesthetics or convenience) will be from about 5 times longer than wide to 20 times longer than wide, for example 6, 7, 8, 9, 10, 12, 15, 17, 18 or 19 times.

Dipsticks for use with highly mobile aqueous liquids suck as water or urine will tend to be shorter than dipsticks for use with more viscous liquids such as saliva or urine. However it is possible to design a dipstick that can be used with both.

The permeable material may be any that permits the reagents to pass from the first zone to the second zone. The skilled worker will be aware of a number of such materials that allow the passage of liquid by capillarity. Many such materials are cellulosic in nature, for example filter paper, cellulose and nitrocellulose membranes. Other suitable materials include polyester, glass fiber, rayon nylon, polydivinylfluoride and the like. A particularly apt material is nitrocellulose. Nitrocellulose films of thickness typically used in the manufacture of dipsticks are apt for use in this invention.

A current choice of nitrocellulose membrane is UniSart CN 140 supplied by Sartorius and equivalent materials from other suppliers. Whatman® Immunopore may be considered for use. The CN stands for cellulose nitrate and the 140 relates to the average wicking rate for deionised water up a 5 cm length of material. Faster and slower wicking materials are available for different forms of the assay device. In the devices of the invention different wicking rates affect assay reaction times. Wicking rates will change depending on the nature of the sample type, for example water and urine may employ relatively faster wicking rates and serum and saliva may employ relatively slower wicking rates. The skilled worker will be aware that standard commercially available materials may be used for such aqueous liquids but that intermediate wicking rates are often suitable for all aqueous samples suspected of containing hapten.

Often more than one type of membrane is used in the device. Aptly two different membrane materials are used, for example glass fiber and nitrocellulose. In such forms the glass fiber is used in the downstream portion, for example in the part where the first zone is located, and the nitrocellulose membrane is used further upstream, for example beyond the first zone and may include the second zone.

The device may also contain a sample collection portion, for example, a projecting highly porous and absorbent section that serves to collect sample to be tested. Such sample collecting means may project from the end on the device downstream of the first zone.

The device may also contain an absorbent material, for example a pad of absorbent material, beyond the second zone to encourage of flow, for example until all the assay sample has been taken up. If the device comprises two layers, then the absorbent material aptly contacts the layer but has minimal contact with the layer. The absorbent pad is aptly of cellulosic material, for example a porous paper pad.

Also forming part of this invention is a permeable strip having a zone containing a non specific antibody against an antibody to a hapten for use in the preparation of a device for analysis the hapten. Such a strip may be used in the manufacture of many devices against different haptens by combining with a strip containing a signal generating means labelled with an antibody against the hapten and a binder therefore as described herein.

(2) Signal Generating Means.

The device may employ any signal generating means that produces a signal when it becomes immobilized in the second zone by the locating means. The skilled worker will be familiar with many such signal generating means. It is possible to employ means that are readable by machine or by eye.

Although any signal generating means useable in lateral flow devises may be employed it is preferred to use one that allows for direct visual detection by eye. Particulate materials such as microparticles of metals such as gold and latexes are well known to the skilled worker and may be used in the devices of this invention. The general and patent literature contains numerous examples of such materials, for example see EP-1416275.

The antibody against the hapten can be attached to such particles in standard manner, for example using the methods described in commercial kits sold for this purpose.

(3) The Hapten.

The device of this invention may be adapted to be used in the assay of a very wide range of haptens. A hapten is a molecule which is too small to itself give rise to an immune response. For the purposes of this document a hapten may be considered to be a molecule of molecular weight less than 900 daltons and greater than 90 Daltons. Aptly the happen has a molecular weight of 100 to 700 Daltons, for example 120 to 400 Daltons, such as about 150, 180, 250 or 300 daltons. Such molecules will normally contain carbon, hydrogen and optionally oxygen and/or nitrogen and sometimes other elements such as sulphur and/or phosphorus. Suitably the hapten may be medicament, hormone, metabolite (for example of a drug of abuse or medicament), toxin, pollutant, substances found in food and drink, substances found in water courses and sewage, substances used for source and product identification or a drug of abuse or other any such hapten that is chosen to be assayed.

Suitable drugs of abuse to be assayed include amphetamine, methamphetamine, 4-methylenedioxyamphetamine (MDA), 3,4-dimethylenedioxymethamphetamine (MDMA, ecstasy). 3,4-methylenedioxyethylamphetamine, tetradydrocanabiniol (THC, cannabis), cocaine, lysergic acid diethylamide (LSD), ketamine, opiodes such as morphine, methadone, Metabolites which occur after ingestion of such drugs are also suitable haptens, for example benzoylecgogonine (BE) which is a metabolite of cocaine.

A particularly suitable hapten is benzoylecgogonine as its presence in a sample derived from a person enables the identification of cocaine use by that person.

Examples of haptens also include phencyclidine, acetaminophen, barbiturates, benzodiazepines, methadone, propoxyphene, tricyclic antidepressants, digoxin, digitoxin, agrochemicals such as those in Agrochemical Desk Reference $2^{nd}$ ED. J. H. Montgomery, CRC Press LLC, 1997, vitamins, natural toxins such as micromycins and mycotocins, hormones such as estradiol, estratriol, ethylidineestradiol, testosterone and the like.

(4) Antibody Against Hapten.

The antibody against the hapten may be a polyclonal or monoclonal antibody. Many antibodies are commercially available and it is one of the great advantages of this invention that many commercial antibodies may be employed rather than having to raise a new antibody for each happen to be employed. However there will be some haptens for which no commercial antibody is available. In such a case the antibody may be produced by the conventional methods known to the skilled worker. The antibody may be the whole antibody or a fragment thereof as long as the locating means is selected to recognise that fragment. Preferably however the antibody is the whole antibody including the Fc portion as the locating means preferably binds nonspecifically to the Fc region of the antibody. The antibody may be of any class and may be obtained from commercial sources or made by the skilled worker using standard methods.

The antibody will be sufficiently specific so that it will not also pick up other haptens that that may occur in a sample in an unwanted manner leading to false positives. This is well understood to the skilled worker as use of specific antibodies is the basis of standard commercial assay systems. The antibody may be selected to be specific epitope found in the test hapten alone or in several closely related haptens that may be tested for, for example as in the case of various amphetamine derivates that may be wished to be identified as a class rather than by individual member.

(5) The Locating Means.

The locating means is preferably not a specific antibody against the antibody against the hapten as this offers a greatly simplified method of putting the invention into operation. The locating means is favourably an antibody against the Fc region of the antibody against the hapten. Alternatively the locating means can be an antibody against the other regions of antibody against the hapten such as the Fab or Fv regions.

The locating means may be a monoclonal or polyclonal antibody but it is particularly preferred that it is a polyclonal antibody.

Preferably the locating means is an anti IgG antibody. Also IgM, IgA, IgE and sub-classes are also envisaged for use. Single chain Fv agents from, for example, camelids and isolated antibody heavy chain are also envisaged for use. The antibodies may be natural of recombinant antibodies.

Non antibody locating means envisaged for use in the invention include molecular imprints (mops), aptamers and substances which non-specifically bind antibody such as protein A and protein G and the like.

The use of a non specific antibody results in considerable benefits in that the difficult to prepare selective antibodies referred to in the prior can be avoided. This benefit is particularly useful when a series of assay devise against different haptens are being produced. The benefit is similarly particularly useful when as assay devise is constructed for use against two or more types type of hapten since a single locating means can be employed.

(5). The Binder.

The binding material against the antibody against the hapten is any which can compete with the hapten for the antibody against the hapten. Generally it is the hapten or a close structural analogue of the hapten covalently bound to a molecule that prevents the binding material binding to the locating means when the material is bound to the antibody against the hapten.

The close structural analogue will be a molecule that retains the same binding sites as the hapten so that it binds to the antibody against the hapten.

Aptly the molecule to which the hapten or close structural analogue is covalently bound is a large molecule, for example has a molecular weight of 5,000 daltons or more. Suitable large molecules include peptides, especially proteins, carbohydrates, and synthetic molecules, for example polymers. Favourably the large molecule is hydrophilic, for example polyethylene glycol or modified polyethylene glycol having terminal amino groups.

Protein molecules that are used in conventional immunoassays to link to hapten or hapten analogues may also be employed, for example keyhole limpet heamocyanin, bovine serum albumen and like proteins. Such proteins can have molecular weights of, for example, 20,000 daltons to 2,000,000 daltons.

Apt blockers include polyethylene glycols of molecular weight 2,000 daltons or more, for example 5,000 daltons or more, 10,000 daltons or more, 15,000 daltons or more, 20,000 daltons or more but generally of molecular weight 60,000 daltons or less, for example 40000 daltons or less, aptly 30,000 daltons or less.

So far identified particularly suitable polyethyleneglycols for use are of molecular weight 20,000 daltons. Suitable commercial source of such a material include Sigma.

For ease in the covalent binding of the hapten or close structural analogue polyethyleglycols (or other synthetic polymer) is modified to have terminal amino groups.

Hapten or hapten analogue may be covalently linked to the large molecule by standard methods of chemical coupling known to the skilled chemist. Typically methods of forming ester, amide, ether or like links can be employed. A method that is presently favoured comprises adding a readily displaceable group to the hapten or hapten analogue, for example a readily displaceable ester group. A presently favoured method is to couple a hydroxysuccinamide group to a carboxylic acid group, for example with a coupling agent such as a carbodiimide such as dicyclohexylcarbodiimide or 1-ethyl-3-(3-dimethylaminopropyl)carbodiimide (EDC). Such reactions can sometimes be carried out in media containing water but it can be useful to employ a dry solvent such as dioxan or dimethylformamide. The active intermediated can then be reacted with the large molecule, for example with an amino or hydroxyl group in such a large molecule. This stage can often be carried out in a solvent such as water, for example in the presence of a buffer or base such as sodium bicarbonate.

Preferably the binding means will have been rendered free of hapten or hapten analogue by exhaustive dialysis. It has been found that a conventional level of dialysis, for example for 24 hours employing common commercial dialyse membrane, leads to assays with a high background that reduces the usefulness, Method successfully employed for rendering the binder free of hapten include dialysis using standard commercial dialysis membrane for ten days or more, for example 20 or 30 days. An alternative and convenient method is to employ spin methods. Most aptly the binding means has two or more, preferably two, hapten or close structural analogues therein. In experiments carried out to date it appears that the divalent blocker produces better results than the monovalent blockers.

Binders can be checked against the antibody on the gold by binding assays known to the skilled worker or by employing in a dip stick with all other components present to check for effectiveness of the assay.

The binding means will move through the dip stick as the aqueous sample permeates through the nitrocellulose or other membrane material. Since it does not bind to the locating means the binder does not have to be fixed to an area of the lateral flow devise and this appears to enhance the effectiveness of the device allowing for a signal line of considerable intensity. This in turn enables the detection of lower concentrations of hapten that is normally the case in dip sticks, for example allowing the assay to be read by eye even in difficult lighting conditions, for example under some street lights.

(6). Control Signal and Quantification.

The device may also be provided with a control means that can serve as confirmation of effective working and/or which can be used to help provide and estimate of measurement of the amount of hapten in the sample.

As a check to make sure that the aqueous liquid is permeating the device and that signal generating means is travelling to the second zone, a second signal generating means and a means for locating it and thereby producing a signal may be employed. The second signal generating means may be labelled with a member of a binding pair and the other member of the binding pair placed in the device on the other side of the second zone from the first zone. The signal generating means need not be the same as the first signal generating means but it is convenient that it is. Thus for example is the signal generating means labelled with an antibody against the hapten is gold particles then the second signal generating means is also conveniently gold particles. Such particles may be essentially identical to those of the first signal generating means or they may be somewhat different.

The binding pair may be any suitable pair such as a ligand and receptor, for example where the one is an antibody and the other a substance to which the antibody binds. However, in is preferred at present to employ biotin and a binding partner therefore such as avadin or and anti-biotin antibody as the members of the pair. It has been found that biotin conjugated to a protein such as bovine serum albumin can be coated on to gold particles and the coated particles applied to the first zone. A line of anti-biotin antibody may be provided beyond the second zone. When in use, the aqueous liquid permeated beyond the second zone and reaches the line of anti-biotin antibody, gold particles labelled with biotin become located and produce a visible signal. This confirms that the device is allowing gold to permeate past the second zone.

Comparison as standard control line to sample line can be used to estimate the concentration of happen in the sample.
(7) Assay Method.

In use the assay may be used in a manner known to the skilled worker. Thus for example a sample suspected of containing the hapten can be introduced to the bottom of the dip stick. This can be in conventional liquid such as saliva or urine or can be produced by wiping an absorbent material across a surface, for example skin, and then transferred to the device in known manner.

EXAMPLES

Example 1

Benzoylecgonine Polyoxyethylene Blocker

Benzoylecgonine (BE) (4 mg) was dissolved in dry dioxin (500 ul) and N-hydroxysuccinamide (NHS) (4 mg) added. 1-Ethyl-3-(3-dimethylaminopropul)carbodiimide hydrochloride (8 mg) was suspended/dissolved in dioxan (1 ml) and immediately added to the mixture. The mixture was shaken at ambient temperature for 2 hours (to form BE-succinamide). To this was added diamino terminated polyethyleneglycol (mol. wt. 20,000) dissolved in 1 ml of 0.1M sodium bicarbonate solution. The solution was left overnight (about 16 hrs) and was then diluted with tris/triton buffer.

The above blocker was dialysed with 5 changes at 4 degrees C. It was then spun in a 10,000 mol. wt. cut-off spin column. The dialysis buffer was 50 mM TRIS buffer (Sigma Cat no. T1503) pH 7.4 plus 0.00 Triton™ X-110 (Sigma cat. No. T9284. The method was as follows. 1) The diBE-PEG sample was placed in a 10,000 mol. wt. cut off dialysis cassette (Pierce Slide-a-lyser Cat. no. 66830. 2) The dialysis cassette was placed in 51 of dialysis buffer. 3) The buffer was changed at 4 hrs. 4). The buffer was changed at 8 hrs and left overnight. 5) Next morning the buffer was changed and left overnight. 6) Step 5 was repeated twice more. Then, 6) 15 ml aliquots of the blocker are placed in Vivaspin® 15 R 10,000 mol wt cut off spin columns (Sartorius cat. No. VS115RH02). 7) These were spun at 3,000 rpm for 30 minutes. 8) The system was topped up to 15 ml with 50 mM TRIS buffer and respun. 9) Step 8 was repeated twice more. 10) The samples were pooled and topped up to the original volume. 11) The blocker is now ready to employ or stored at 4 degrees C. prior to use.

Example 2

Aldicarb-PEG Blocker

Aldicarb acetate ethyl ester was synthesised and then hydrolysed to give a yellow oil which was a carboxylic acid substituted analogue of aldicarb (see Siew et. al., International Journal Environ. Anal. Chem 83, 417-426). The aldicarb-COOH (2.9 mg) was dissolved in dioxin (600 ul). To this solution was added NHS (2.9 mg) in dioxin (150 um). To the resulting mixture was added N'N'-dicyclohexyl-carbodiimide (5.8 mg) in dimethylfomamide (580 ul) and the mixture left shaking for 2 hours. At the end of this time a solution of diamino-PEG (as Ex. 1) (12.4 mg) dissolved in 0.1 mM sodium bicarbonate solution (1.24 ml). The mixture was left the stir overnight. This was diluted with tris/triton buffer and dialysed as set out in ex. 1.

Example 3

Dip-Stick.

Two lines are deposited on a 30 cm length of nitrocellulose using an IsoFlow unit. The nitrocellulose was UniStart CN 140 from Sartorius. A test line pf polyclonal goat anti mouse IgG which binds to Fc regions on antibodies non-specifically (Sigma cat. No. M4280) diluted to 50% in phosphate buffered saline was employed. A control line of monoclonal anti-biotin (Bio-Desige cat no H20098M) was also deposited. The control line was deposited 13 mm from the leading edge of the nitrocellulose and the test line was deposited 17 mm from the leading edge of the nitrocellulose.

The IsoFlow deposition parameters were as follows.

| Setup move menu | | Setup pump menu | |
|---|---|---|---|
| Parameter | Setting | Parameter | Setting |
| Dispense Distance | 300 mm | Dispense Rate | 0.100 ul/mm |
| Dispense speed | 50 mm/s | Aspirate Rate | 8 ul/s |
| Return Speed | 300 mm/s | Start pause | −0.10 s |
| Start position | 0 mm | Stop pause | −0/10 s |
| Return pause | 1.00 s | Syringe size | 100 ul |
| Lower nozzles | 0.50 s | Inlet volume | 40 ul |
| Raise nozzles | 1.00 s | Outlet volume | 60 ul |

Following deposition each length of material was examined for faults and if present were marked and discarded post assembly. Once examined and while the deposited lines were still visible the bands were dried using a hair drier set to maximum. Following drying the material was stored in a dry environment.

The specific anti BE line was layed down. Monoclonal antibody specific to BE (East Coast Biologicals cat. No. P01-99-11M-P), pre-diluted to 300-350 ug/ml in purified eater, was conjugated to BioAssay Works gold (BAW gold conjugation kit). Once conjugated the gold can be stored at 2-8 C prior to spraying on a glass fiber (or nitrocellulose) membrane.

To form a control biotin was conjugated to bovine serum albumin and coated onto) OD 1.0 colloidal gold supplied by British Biocell International. Incubation of a 1 mg/ml solution of the conjugated biotin-BSA to the gold was effected whist mixing for 30 minutes at ambient temperature. Following incubation the colloidal gold was centrifuged at 13,000 rpm for 6 minutes, supernatant was discarded and the pellet resuspended in tris buffered saline pH 8.2 containing Triton™ X-110 and 1% BSA at a concentration equivalent to OD 0.5.

Once prepared the colloidal gold conjugates were mixed in the ratio 1 part control line gold to one part specific BE marker gold and 1 part of sucrose solution in tris buffered saline pH 8.2.

The membrane (conjugate release pad) was 27 mm wide and supplied on a reel (Whatman, Standard 14 Part Number 8133-2750). It was cut into 30 cm lengths for spraying.

The gold was air brushed onto the membrane using the IsoFlow using the parameters given above except the setup move menu dispense speed was 30 mm/s and the setup pump dispense rate was 0.8 ul/mm. The gold was sprayed at a height of 5 mm above the conjugate pad at 4 psi and 10 mm from the leading edge of the pad.

Once deposited the band of material were dried for three hours at 37 C in an incubator before being stored in a dry environment.

The binding material was di-BE-polethyleglycol (conjugated through amino groups) as described in example 1. This material had been scanned from 200-500 nm on a spectrophotometer to confirm freedom from unconjugated BE.

The binding material was diluted 1:1 with tris buffered saline pH 8.2 containing Triton™ X-110 and 1% BSA. The mixture was sprayed onto the conjugate pad 20 mm from the leading edge using the IsoFlow using the parameters set out above except that the setup pump dispense rate was 0.4 µg/mm. Following deposition, the material was dried for 3 hours at 37 C in an incubator before being stored in a dry environment.

Once the components were prepared they were assembled into a working test. All components were mounted onto self adhesive cards (G+L Precision). Cards were 0.01 inch white vinyl with GL-187 adhesive, 75 mm by 3000 mm.

The nitrocellulose membrane was applied to the adhesive first, with leading edge 25 mm from the base of the card. To the top of the card a strip of absorbent paper was added to form a sink (Whatman, CF6 Part Number 8116-2750). This was supplied as a reel of material 27 mm wide so there was a 2 mm overlap with the nitrocellulose. The conjugate pad was then applied to the base of the pad with a 2 mm overlap with the nitrocellulose.

The assembled cards were then cut into 5 mm strips ready for use.

When tested the dip sticks were able to detect BE in samples of spiked urine at concentrations of 10 ng/ml (lowest concentration in test) 100 ng/ml, 300 ng/ml, 1,000 ng/ml and 10,000 ng/ml demonstrating increasing intensity of the detection line was concentration increased.

Example 4

Preparation of Various Blockers for Use in Assay for Use in Methamphetamine Assay
Chemistry

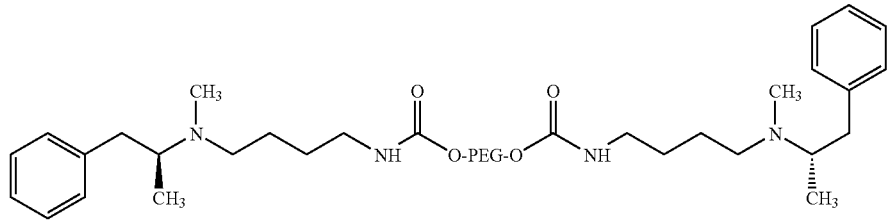

To α,ω-di-succinimidyl ester polyethylene glycol) Mol wt 20,000 (9.9 mg, 4.95×10$^{-4}$ mmol) in dioxan (1 ml) followed by di-isopropylethylamine (0.02 ml) was added N-(4-aminobutyl)-N-methyl-N-[(1S)-1-methyl-2-phenylethyl]amine (5.0 mg, 0.0227 mmol) in dry dioxan (0.2 ml). The reaction mixture was shaken for 23 hours at 20-25° C. The mixture was diluted then dialyzed against 50 mM of Tris buffer at pH 7.4 (4×5 L) using at 10,000 molecular weight cut off membrane. The resulting solution GRD-55 (6.204 g) was slightly hazy in appearance.

Methamphetamine BSA, Methamphetamine KLH

To BSA (26.4 mg) in water (4 ml) was added NHS (21.3 mg, 0.18 mmol) in water (0.5 ml) followed by EDC (40 mg, 0.193 mmol) in water (0.5 ml). The mixture was shaken for 15 minutes at 20-25° C. N-(4-aminobutyl)-N-methyl-N-[(1S)-1-methyl-2-phenylethyl]amine (1.8 mg, 0.0081 mmol) in dioxan (0.2 ml) was added followed by di-isopropylethylamine (0.02 ml). The mixture was shaken for 18 hours at 20-25° C.

To KLH (20 mg) in water (4 ml) was added NHS (24 mg, 0.21 mmol) in water (0.5 ml) followed by EDC (39 mg, 0.189 mmol) in water (0.5 ml). The mixture was shaken for 15 minutes at 20-25° C. N-(4-aminobutyl)-N-methyl-N-[(1S)-1-methyl-2-phenylethyl]amine (1.8 mg, 0.0081 mmol) in dioxan (0.2 ml) was added followed by di-isopropylethylamine (0.02 ml). The mixture was shaken for 18 hours at 20-25° C.

The above materials were dialysed against 50 mM Tris buffer at pH 7.4 containing sodium azide using a 10,000 molecular weight cut off membrane. BCA protein assay gave concentrations of 2.2 mg/ml and 1.9 mg/ml respectively.
Chemistry

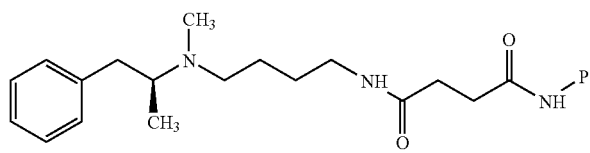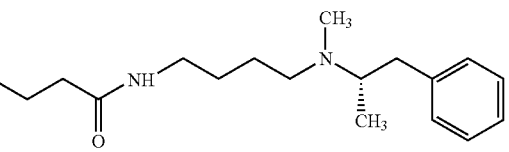

To N-(4-aminobutyl)-N-methyl-N-[(1S)-1-methyl-2-phenylethyl]amine (10.4 mg, 0.0472 mmol) in dioxan (0.5 ml) was added 0.41 ml of a succinic anhydride (6.1 mg in 0.5 ml dioxin). The reaction mixture was heated at 70° C. for 18 hours.
Coupling to PEG
DIC Method
To 0.455 ml of the above solution was added NHS (14.8 mg, 0.128 mmol) in dioxin (0.1 ml) followed by DIC (18.5 μl, 0.119 mmol). The mixture was shaken for 20 minutes then added O,O'-bis(2-aminoethyl)-polyethyleneglycol 20,000 (6.0 mg, $3 \times 10^{-4}$ mmol) in dioxan (0.5 ml). The reaction was shaken for 18 hours at 20-25° C. The solution was dialysed against 4×5 L of 10% ethanol/water using a 10,000 molecular weight cut off membrane to yield 5.678 g of conjugate solution.
BOP Method
To O,O'-bis(2-aminoethyl)-polyethyleneglycol 20,000 (5.9 mg, $2.9 \times 10^{-4}$ mmol) in dioxan (0.4 ml) was added di-isopropylethylamine (0.045 ml, 0.236 mmol) and BOP (53 mg, 0.119 mmol) dissolved in dioxan (0.4 ml), DMF (0.6 ml). 0.455 ml of the succinate solution was added and the mixture shaken for 18 hours at 20-25° C. Dialysis was as above and yielded 11.205 g of solution.

Example 5

Preparation of Blocker for Use in Amphetamine Assay
Chemistry

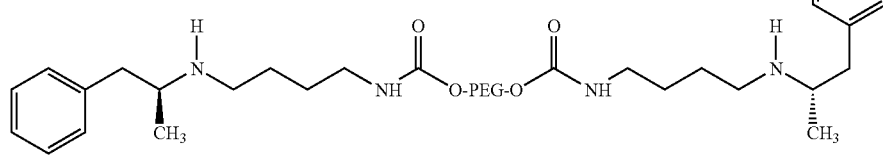

To α,ω-di-succinimidyl ester poly(ethylene glycol) Mol wt 20,000 (17.6 mg, $8.8 \times 10^{-4}$ mmol) in dioxan (0.4 ml), NHS (14.7 mg, 0.127 mmol) in dioxan (0.2 ml) was added followed by DIC (18.5 μl, 15 mg, 0.119 mmol). The reaction mixture was shaken for 48 hours. N-[(1S)-1-methyl-2-phenylethyl]butane-1,4-diamine (21 mg, 0.101 mmol) in dioxan (0.2 ml) was added followed by di-isopropylethylamine (0.036 ml). The reaction mixture was shaken for 24 hours at 20-25° C. The mixture was then dialyzed against deionised water con-taining 10% methanol (4×5 L) using a 10,000 molecular weight cut off membrane. The resulting solution GRD-89 (16.082 g) was slightly hazy.

Amphetamine BSA

To BSA (24.8 mg) in water (4 ml) was added NHS (22.2 mg, 0.193 mmol) in water (0.5 ml) followed by EDC (41 mg, 0.199 mmol) in water (0.5 ml). The mixture was shaken for 15 minutes at 20-25° C. N-[(1S)-1-methyl-2-phenylethyl]butane-1,4-diamine (2.7 mg, 0.013 mmol) in dioxan (0.2 ml) followed by di-isopropylethylamine (0.02 ml). The mixture was shaken for 18 hours at 20-25° C. The above material was dialysed against 50 mM Tris buffer at pH 7.4 containing sodium azide using a 10,000 molecular weight cut off membrane. BCA protein assay after dialysis gave a concentration of 1.6 mg/ml.

Example 6

Preparation of Blocker for Use in Aldicarb Assay
Chemistry

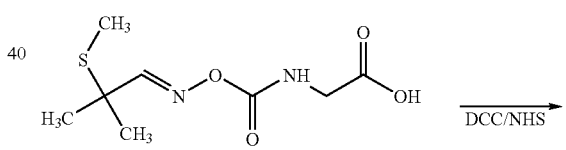
DCC/NHS

-continued

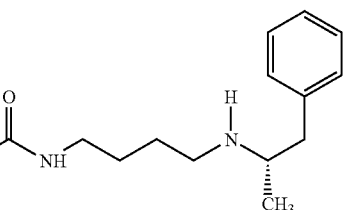
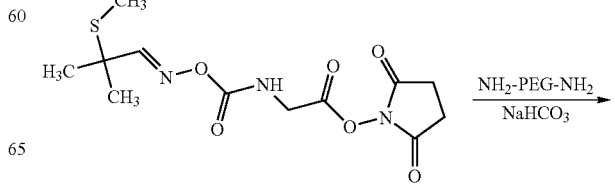
NH$_2$-PEG-NH$_2$
NaHCO$_3$

-continued

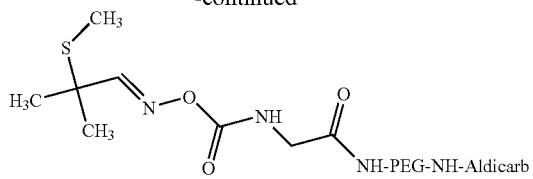

To aldicarb carboxylic acid (11.0 mg, 0.047 mmol) in dry dioxan (2.2 ml) was added NHS (11.5 mg, 0.10 mmol) in dry dioxan (0.7 ml) followed by DCC (29.0 mg, 0.14 mmol) in dry dioxan (2.1 ml). The reaction mixture was shaken for 23 hours at 20-25° C.

PEG 6000 Molecular Weight

To 6K PEG-diamine (5.0 mg, $8.3\times10^{-4}$ mmol) in 0.1M $NaHCO_3$ (1.5 ml) was added activated aldicarb carboxylic acid solution prepared as above, (1.67 ml, 0.0156 mmol) The mixture was then shaken for 18 hours.

PEG 10,000 Molecular Weight

To 10K PEG-diamine (8.1 mg, $8.1\times10^{-4}$ mmol) in 0.1M $NaHCO_3$ (1.5 ml) was added activated aldicarb carboxylic acid solution (1.67 ml, 0.0156 mmol) The mixture was shaken for 18 hours.

PEG 20,000 Molecular Weight

To 20K PEG-diamine (14.9 mg, $7.45\times10^{-4}$ mmol) in 0.1M $NaHCO_3$ (1.5 ml) was added activated aldicarb carboxylic acid solution (1.67 ml, 0.0156 mmol). The mixture was shaken for 18 hours.

The above materials were dialysed separately against 50 mM Tris buffer (5×5 L) at pH 7.4 containing sodium azide using a 2,000 molecular weight cut off membrane.

Dialysis yielded 9.248 g of solution for the 6K PEG (GRD-54-1), 8.955 g for the 10K PEG (GRD-54-2) and 8.800 g for 20K PEG (GRD-54-3).

Lateral Flow Data

With the 20,000 dalton PEG-Aldicarb assigned 100% blocking efficiency, 10,000 and 6,000 PEG-Aldicarb were 90% and 80% respectively.

Example 7

Preparation of Various Blockers from Diamino Terminated Polyethylene Glycols

Diamino-PEG-Blockers

All blockers were originally prepared as follows using a 10 fold excess of antigen to PEG-NH2 groups. The PEG-antigen complexes were originally dialysed in Tris-Triton buffer as given below as that was the buffer used in our ELISA and Dipstick assays.

The Triton has a large absorbance at 280 nm which makes it very difficult to analyse the resulting conjugates. We now therefore routinely dialyse the conjugates in 10-25 mM Sodium Phosphate buffer pH 7.5 (or even in water). This makes analysis of the final conjugates much easier Benzoylecgonine to $PEG(NH_2)_2$ Benzoylecgonine (BE) is the metabolite of cocaine, antibodies to BE cross react 100% with Cocaine.

BE 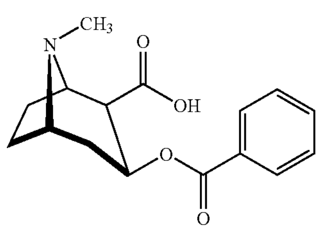 4 mg benzoylecgonine (BE) is dissolved in 500 ul dry dioxan and this has 4 mg N-Hydroxysuccinimide (NHS) added to it in another 500 ul dioxan. 8 mg of 1-Ethyl-3-[3-dimethylaminopropyl]carbodiimide hydrochloride (EDC) is then suspended in 1 ml dioxan (does not completely dissolve) and immediately added to the BE/NHS mix. Stable BE-NHS esters are produced as the mixture is left shaking at ambient temp for 2 hours. After 2 hours 11 mg of $PEG-(NH_2)_2$ dissolved in 1 ml of 0.1M Sodium Bicarbonate is added. The BE-NHS residues couple via amide bonds to the $PEG-NH_2$ groups with the regeneration of free NHS. This is left with shaking o/n for $PEG-(NH—CO-BE)_2$ complexes to form. The reaction mix is then diluted to 11 ml with Tris/Triton buffer and dialysed for 2-3 days against 5 l Tris/Triton buffer with 2-3 changes of buffer a day Notes. Has to be EDC which is a water soluble carbodiimide, other carbodiimides do not work, possibly due to BE crystals containing water. Amount of BE added is approx a 10 fold excess to amount required to bind to both ends of the PEG.

BE MW is 365×2=730 mg BE=20,000 mg PEG 36.5 ug of BE is required to bind to both ends of 1 mg PEG.

4 mg BE=11 mg PEG at 10× excess $PEG-(NH_2)_2$ was added in Bicarbonate (pH approx 8.4) to maximise formation of amide bonds between BE-NHS ester group and PEG amine group. Tris/Triton buffer is 50 mM Tris-HCl buffer pH 7.4 containing 0.05% Triton™ X-110.

Aldicarb to $PEG(NH_2)_2$

Aldicarb acetate ethyl ester was synthesised and this was then hydrolysed to give a yellow oil which was a carboxylic acid substituted analogue of aldicarb (as previously described, Siew et al, *Intern. J. Environ. Anal. Chem.* 83, 417-426).

Aldicarb-COOH 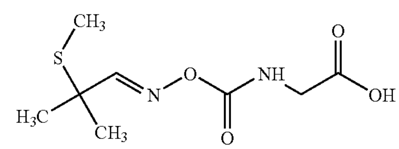 2.9 mg Aldicarb-COOH was dissolved in dioxan (600 ul) and 2.9 mg NHS was added in another 150 ul dioxan. 5.8 mg N,N'-Dicyclohexyl-Carbodiimide (DCC) dissolved in 580 ul Dimethylformamide (DMF) was added and the mixture left shaking for 2 hour to form Aldicarb-NHS esters. After the 2 hours 12.4 mg $PEG-(NH_2)_2$ dissolved in 1.24 ml of 0.1M Sodium Bicarbonate was added the mixture was left to shake o/n.

This was then diluted to 12.4 ml with Tris/Triton buffer and dialyse for 2-3 days against 5 l Tris/Triton buffer with 2-3 changes of buffer a day Note; —Again a 10 fold excess of Aldicarb to $PEG-(NH_2)_2$ Aldicarb acid MW 234 $PEG-(NH_2)_2$ MW 20,000

Therefore 468 mg Aldicarb=20,000 mg PEG (2 reactive amines)

23.4 ug=1 mg PEG 234 ug=1 mg at 10× excess 2.9 mg=12.4 mg PEG

Paraquat-$PEG(NH_2)_2$

To 6 mg Paraquat-hexanoic acid derivative (see Anal Chem 58, 1866-1873) in 400 ul water was added 6 mg NHS in 600 ul pure water. 30 mg EDC was then added to the paraquat/NHS mix. This was left for only 15 min as Paraquat-NHS is unstable in water (NHS esters are stable in organic solution but paraquat is not soluble in organics) and 16 mg PEG- (NH$_2$)$_2$ was added in 1.6 ml 0.1M Sodium Bicarbonate. This was left o/n, then made up to 16 ml with Tris/Triton buffer and dialysed as above.

Paraquat hexanoic acid

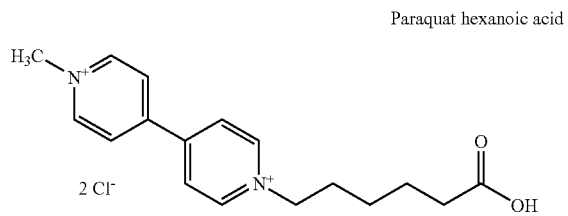 [SMILES: C[n+]1ccc(-c2cc[n+](CCCCCC(=O)O)cc2)cc1 ; "2 Cl-"]

Chlorpyrifos-PEG(NH$_2$)$_2$

Chlorpyrifos carboxylic acid

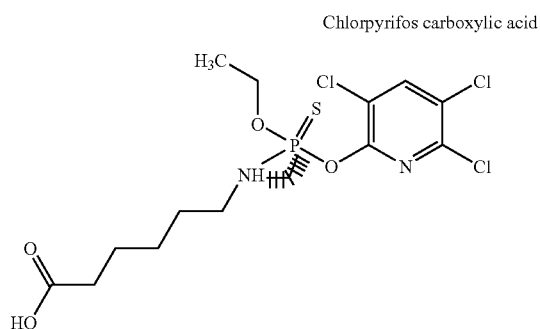 [SMILES: CCOP(=S)(NCCCCCC(=O)O)Oc1nc(Cl)c(Cl)cc1Cl]

5 mg Chlorpyrifos-carboxylic acid derivative (Hapten 2, Bull. Korean. Chem. Soc 2002, 23, 481-487.) was dissolved in 1 ml DMF followed by the addition of 5 mg NHS in 0.5 ml DMF and 5 mg DCC in 0.5 ml DMF. This was shaken for 2 hr for Chlorpyrifos-NHS esters to form. 11.5 mg PEG-(NH$_2$)$_2$ was then added in 1.15 ml 50 mM Sodium Phosphate pH 7.5. (Chlorpyrifos hydrolyses rapidly at pH>8.0 so you do not couple it to PEG-(NH$_2$)$_2$ in bicarbonate As done with the other haptens)

Leave o/n with shaking, make up to 11.5 ml final volume with Tris/Triton and again dialyse as above Note; —We now dissolve the PEG-(NH$_2$)$_2$ in 2 mls of dioxan (instead of buffer). The chlorpyrifos-NHS will stably couple to the PEG amine groups in this organic solution. Dialysis is then carried out in Phosphate buffer at pH 7.0. This maximises the stability of the PEG-Chlorpyrifos conjugates Summary Protocol for Bioassay Works 40 nm Colloidal Gold Assessment Antibody concentration used can be between 0.3-1.5 mg/ml it can also be either Whole or Fab fragments. You should also be able to use ScFv coated on gold as well
Method:
Dilute the 40 nm Colloidal gold one in three (=OD 5.0) in ultrapure water.
Place 0.1 mL of the gold sol into ten labelled test tubes and add 0.2 mL of ultrapure water to each tube.
Prepare in separate labelled tubes the following mixtures of buffers in μL:

| Tube Number | pH | Buffer A | Buffer B |
| --- | --- | --- | --- |
| 1 | 5.4 | 18 | 2 |
| 2 | 6.6 | 16 | 4 |
| 3 | 7.3 | 12 | 8 |
| 4 | 7.8 | 8 | 12 |
| 5 | 8.2 | 4 | 16 |

| Tube Number | pH | Buffer C | Buffer D |
| --- | --- | --- | --- |
| 6 | 8.4 | 10 | 0 |
| 7 | 8.8 | 16 | 4 |
| 8 | 9.2 | 12 | 8 |
| 9 | 9.6 | 8 | 12 |
| 10 | 10.1 | 4 | 16 |

Transfer 3 μL of each buffer to the correspondingly numbered colloidal gold containing tube.
Gently vortex mix.
Add 15 μL of the antibody (250-350 μg/mL) to each tube.
Gently vortex mix.
Incubate static for 30 mins.
Add 30 uL of the supplied blocking solution to each tube.
Gently vortex mix.
Gold is ready for testing.

Membrane Deposition

Test line deposition for whole antibody uses α mouse IgG (Fc specific)
Test line for Fab fragments uses α mouse IgG (fab specific)
Deposition of MAb α-biotin as Control line.
Materials:
MAb α-biotin Bio Design
Goat α mouse IgG (Fc specific) Sigma 1 mg/ml
Goat anti mouse IgG (Fab specific)
Sartorius Membrane Unisart CN 140
10 mM PBS
Method:
Standard machine programme:
Line Deposition
Setup Move Menu

| Parameter | Setting |
| --- | --- |
| Dispense Distance | 300 mm |
| Dispense Speed | 50 mm/s |
| Return Speed | 300 mm/s |
| Start position | 0 mm |
| Return Pause | 1.00 s |
| Lower Nozzles | 0.50 s |
| Raise Nozzles | 1.00 s |

Setup Pump Menu(s)

| Parameter | Setting |
| --- | --- |
| Dispense Rate | 0.100 μL/mm |
| Aspirate Rate | 8 μL/s |
| Start Pause | −0.10 s |
| Stop Pause | −0.10 s |
| Syringe Size | 100 μL |
| Inlet Volume | 40 μL |
| Outlet Volume | 60 μL |

MAb α-biotin diluted 1 mg/ml in PBS and the Goat α mouse IgG (Fc specific) diluted 1 mg/ml in PBS.
30 cm bands of nitrocellulose cut from the reel and a line drawn on the reverse (Mylar®-backed side 3 mm from either edge—designated the top). Bands transferred and lines drawn one band at a top ensuring orientation (black line on the top furthest away from operator). Six, 30 cm bands were deposited in total. After three bands deposited these are dried using the hair dryer.

Test line Can vary from 5 mm from the base of the strip to 13 mm and the control line from 10 mm to 18 mm from the base of the strip.

Membrane stored as bands in air tight container with silica gel.

Conjugate Pad Spraying

Aim:
Deposition gold, buffer and blocker.
Materials:

| | |
|---|---|
| Conjugated gold | Analyte conjugated to gold |
| Control gold | Biotin BSA conjugated to gold. |
| Assay Buffer | Trizma Base 50 mM plus NaCL 154 mM pH 8.2 |
| With | 1% (w/v) Bovine Serum Albumin (BSA) |
| | 0.1% (v/v) Triton ™ X-100 |
| | 0.1% (w/v) NaN$_3$ |
| Assay Block | Analyte conjugated to Bis PEG 20,000 concentration adjusted to concentration to give maximum of 4 passes. |
| 50% sucrose solution. | |
| ACS water. | |

Spray Positions and Spray Order
1$^{st}$ Gold conjugate position—
  Gold sprayed in middle of conjugate pad 2 passes.
2$^{nd}$ Buffer position
  Buffer sprayed 5 mm from bottom of conjugate pad 2 passes
3$^{rd}$ Blocker position—
  Blocker sprayed 5 mm from top of conjugate pad 4 passes two on each side on top of each other. Dry using hair dryer between each pass.
Method
30 cm bands of conjugate pad are cut from the reel. The right hand bottom corner is cut to identify the bottom edge of the pad.

Biotin gold and analyte gold conjugates are mixed 1:2 to this is added 1 part ACS water and 1 part 50% sucrose.

This is now ready for spraying using the standard machine settings see below.

Dry using low setting on hair dryer between each line deposited and 3 hrs at 37° C. Between spraying of buffer and blocker.

Standard machine programmes:

30 cm bands of conjugate pad are cut from the reel. The right hand bottom corner is cut to identify the bottom edge of the pad.
Further Commentary Commercial antibodies may be employed when available. If no antibodies easily obtained commercially they may be raised by standard methods such as the following.

The antibody against chlorpyrifos was raised by the following schedule: day 0, primary immunisation 100 μg in Complete Freund's; day 16, first boot 100 μg in Incomplete Freund's; day 28 second boost 100 μg Incomplete Freund's; day 63 third boost in Incomplete Freund's; day 112 fourth boost for fusion; day 116 fusion. The immunogen was chlorpyrifos-KLH conjugate mice spleens were fused with myeloma line NS-1.

The antibodies against aldecarb were made on the same protocol using aldecarb-BSA conjugate.

Antibodies against methamphetamine were made using a mixture of amphetamine BSA and methamphetamine BSA. Four immunisations of 100 μg, the first in Freund's Complete and the other three in Freund's Incomplete were used. Spleens were fused to NS1 myeloma and screened against amphetamine and methamphetamine. The antibodies were very sensitive to methamphetamine and about 1000 fold less sensitive for amphetamine.

Commercial antibody against amphetamine was used.

The antibody against paraquat was raised by immunising with paraquat-KLH on the following schedule: day 0, primary immunisation 100 μg in TiterMax® Gold; day 15 first boost 100 μg in TiterMax® Gold; day 28 second boost 100 μg in TiterMax® Gold; day 37 fourth boost for fusion; day 41 fusion. Mouse spleens were fused with myeloma line NS-1. Clones were screened using competitive Eliza and positives selected, single cell cloned and screened to stable clone.

The immunogen used reflect the binding material so that the antibodies produced will potentially bind both to the hapten and the binding material. It is desired for a competition to be able to take place between these agents in the liquid phase as it travels throughout the device.

Hence, in order to produce the immunogen for raising antibodies to methamphetamine, methamphetamine is linked to a —(CH$_2$)$_4$NH group by reaction with 4-bromobutylphthalamide followed by hydrolysis. This amine is then coupled to BSA using a water soluble carbodiimide such as N-(3_dimethylaminopropyl)-ethyl-N-carbodiimide (EDC).

Similarly the paraquat antibody is raised using a paraquat conjugate via a —(CH$_2$)$_6$NH$_2$ linker (which is commercially available). Aldecarb conjugate can be derived by activation of

| | Parameter | Setting Gold | Block | Buffer |
|---|---|---|---|---|
| Move menu | Dispense Distance | 300 mm | 300 mm | 300 mm |
| | Dispense Speed | 30 mm/s | 30 mm/s | 30 mm/s |
| | Return Speed | 300 mm/s | 300 mm/s | 300 mm/s |
| | Start position | 0 mm | 0 mm | 0 mm |
| | Return Pause | 1.00 s | 1.00 s | 1.00 s |
| | Lower Nozzles | 0.50 s | 0.50 s | 0.50 s |
| | Raise Nozzles | 1.00 s | 1.00 s | 1.00 s |
| Pump menu | Dispense Rate | 0.8 μL/mm | 0.8 μL/mm | 0.8 μL/mm |
| | Aspirate Rate | 8 μL/s | 8 μL/s | 8 μL/s |
| | Start Pause | −0.10 s | −0.10 s | −0.10 s |
| | Stop Pause | −0.10 s | −0.10 s | −0.10 s |
| | Syringe Size | 250 μL | 250 μL | 250 μL |
| | Inlet Volume | 40 μL | 40 μL | 40 μL |
| | Outlet Volume | 60 μL | 60 μL | 60 μL | the aldecarb acid with NHS (N-hydroxysuccinamide) and reacting this with the protein, for example at pH 9. With chlorpyrifos (also called herein chlorpyriphos), the analogue with the six carbon linker is obtainable by reaction with aminocaproic acid, activated with NHS and coupled to the protein.

The skilled worker is familiar with the chemistry required once the principles of the assay are read herein. The concept of close structure analogue is similarly well understood by the skilled worker as very many diagnostic systems rely on this concept generally in order to work. The analogue will contain sufficient structural features in common with the hapten to be able to compete with it for sites on the antibody; thus the relevant epitope will be preserved. Such analogues are often esters of acid groups or esters or amides of hydroxyl or amino groups in the hapten or compounds wherein a hydroxyl group or amino group are substituted by alkyl or substituted alkyl groups or the like. The skilled worker will be fully familiar with the concept.

The invention claimed is:

1. An assay device for identifying the presence of a hapten, comprising a permeable
    material such that when an aqueous liquid is contacted with a first part of the permeable material it permeates to a second part of the permeable material, said permeable material having a first zone and a second zone disposed so that when the aqueous liquid is contacted with the first part of the permeable material it passes first through the first zone and then into the second zone as it permeates to the second part of the permeable material;
    said first zone comprising a signal generating means labeled with an antibody against a hapten to be identified;
    said first zone further comprising a binding material for said antibody against the hapten to be identified, wherein the binding material is a hapten or a close structural analogue thereof bound to a large molecule that prevents binding to a locating means when the binding material is bound to the antibody against the hapten;
    said second zone comprising said locating means for said antibody against the hapten to be identified such that the locating means binds to the antibody present on the signal generating means labelled with an antibody which has bound the hapten to be identified but does not bind to an antibody present on the signal generating means which has bound the binding material for said antibody against the hapten to be identified;
    the signal generating means being such that a signal is generated on binding to said locating means;
    wherein the locating means is not a specific binder for the antibody against the hapten to be identified.

2. The device of claim 1, wherein the locating means is an antibody against the Fc region of the antibody against the hapten to be identified.

3. The device of claim 1, wherein the binding material for the antibody against the hapten to be identified is free of unbound hapten and/or hapten analogue.

4. The device of claim 1, wherein the large molecule is a synthetic hydrophilic molecule of molecular weight greater than 2000.

5. The device of claim 1, wherein the binding material has two haptens or close structural analogues thereof bound to a large molecule.

6. The device of claim 1, in the form of a dip stick.

7. The device of claim 1, wherein the locating means is an antibody against the Fab region of the antibody against the hapten to be identified.

8. The device of claim 1, wherein the locating means is a polyclonal antibody.

9. The device of claim 1, wherein the signal generating means is a plurality of microparticles.

10. The device of claim 1, wherein the signal generating means is a plurality of microparticles and wherein the microparticles are latex.

11. The device of claim 1, wherein the signal generating means is a plurality of microparticles and wherein the microparticles are gold microparticles.

12. The device of claim 1, wherein the large molecule is of molecular weight 5000 daltons or more.

13. The device of claim 1, wherein the large molecule is a hydrophilic synthetic molecule.

14. The device of claim 1, wherein the large molecule is a hydrophilic synthetic molecule comprising a polyethylene glycol.

15. The device of claim 1, wherein the large molecule is a hydrophilic synthetic molecule comprising a polyethylene glycol having a molecular weight of 5000 to 60000 daltons.

16. The device of claim 1, wherein the large molecule is a hydrophilic synthetic molecule comprising a polyethylene glycol having a molecular weight of 10000 to 40000 daltons.

17. The device of claim 1, wherein the large molecule is a hydrophilic synthetic molecule comprising a polyethylene glycol having a molecular weight of 20000 to 30000 daltons.

18. The device of claim 1, wherein the large molecule is a hydrophilic synthetic molecule comprising a polyethylene glycol having terminal amino groups.

19. The device of claim 1, wherein the hapten to be identified is a drug of abuse.

20. The device of claim 1, wherein the hapten to be identified is a drug of abuse selected from: cocaine, amphetamine or methamphetamine.

21. The device of claim 1, wherein the hapten to be identified is an environmental pollutant.

22. The device of claim 1, wherein the hapten to be identified is an environmental pollutant selected from: aldicarb, paraquat or chlorpyraphos.

23. The device of claim 1, wherein the hapten to be identified is a natural toxin.

24. The device of claim 1, wherein the hapten to be identified is a mycotoxin.

25. The device of claim 1, wherein the hapten to be identified is of molecular weight of 120 to 400 daltons.

26. The device of claim 1, wherein the large molecule is a hydrophilic synthetic molecule comprising a polyethylene glycol having a molecular weight of 5000 to 60000 daltons, and wherein the hapten to be identified is a mycotoxin.

27. The device of claim 24, wherein the large molecule is a hydrophilic synthetic molecule comprising a polyethylene glycol having a molecular weight of 10000 to 40000 daltons.

28. The device of claim 11, wherein the hapten to be identified is a mycotoxin.

29. The device of claim 3, wherein the hapten to be identified is a mycotoxin.

30. The device of claim 3, wherein the large molecule is a hydrophilic synthetic molecule comprising a polyethylene glycol having a molecular weight of 10000 to 40000 daltons.

31. The device of claim 30, wherein the hapten to be identified is a mycotoxin.

* * * * *

UNITED STATES PATENT AND TRADEMARK OFFICE
CERTIFICATE OF CORRECTION

PATENT NO. : 8,389,296 B2  Page 1 of 1
APPLICATION NO. : 12/593262
DATED : March 5, 2013
INVENTOR(S) : Self et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 308 days.

Signed and Sealed this
First Day of September, 2015

Michelle K. Lee
*Director of the United States Patent and Trademark Office*